United States Patent [19]

Sanderson et al.

[11] Patent Number: 4,556,730

[45] Date of Patent: Dec. 3, 1985

[54] ESTER COMPOUNDS FROM 5-VINYL-2-NORBORNENE

[75] Inventors: John R. Sanderson; Edward C. Y. Nieh; Lewis W. Watts, Jr., all of Austin, Tex.

[73] Assignee: Texaco Inc., White Plains, N.Y.

[21] Appl. No.: 423,413

[22] Filed: Sep. 24, 1982

[51] Int. Cl.[4] .................... C07C 69/16; C07C 69/28
[52] U.S. Cl. .................. 560/256; 252/56 S; 252/364; 560/246; 560/247
[58] Field of Search ............... 560/256, 246; 568/820

[56] References Cited

U.S. PATENT DOCUMENTS 3,239,539  3/1966  Bartlett et al. .................. 560/256
3,646,113  2/1972  Rick et al. ....................... 560/256

Primary Examiner—Vivian Garner
Attorney, Agent, or Firm—R. A. Kulason; Jack H. Park; Kenneth R. Priem

[57] ABSTRACT

Novel compounds made from the reaction of 5-vinyl-2-norbornene with carboxylic acid anhydrides in the presence of oxygen are described. The process to make these novel esters is preferably conducted at a temperature in the range from about 50° to 150° C. and in the presence of a catalyst. A transition metal borate catalyst is preferred. Such ester compounds are potentially useful plasticizers, lubricants, solvents and fuel additives.

1 Claim, No Drawings

ESTER COMPOUNDS FROM 5-VINYL-2-NORBORNENE

CROSS-REFERENCE TO RELATED APPLICATION

This application is related to patent application Ser. No. 402,664, filed July 28, 1982, now Pat. No. 4,451,668, which relates to the production of alkane acetates from alkenes using transition metal borate catalysts.

This application is also related to patent application Ser. No. 423,412, filed of even date, concerning other novel cyclic ester compounds.

BACKGROUND OF THE INVENTION

1. Field of the Invention

The invention is related to novel ester compounds, and is particularly related to novel cyclic ester compounds having one or more ester functionalities.

2. Description of Methods and Compounds Relevant to the Invention

Various esters, also known as acetates, have been made by a number of different methods, many of which use olefins as the starting material. For example, U.S. Pat. No. 2,497,408 suggests the production of propylene glycol diacetate from propylene oxygen and acetic acid over a metal acetate catalyst in which the metal is lead or iron in combination with an alkali earth metal acetate. Another example of this approach is U.S. Pat. No. 3,403,175 where olefins in oxygen are reacted in the presence of a reaction medium consisting of carboxylic acid and anhydrides with no catalyst to produce glycol diesters. Acyloxy compounds may be produced by the reaction of olefins with the metal salt of a carboxylic acid in an aqueous solution if electric current is passed through the solution, according to the method of U.S. Pat. No. 3,453,189. U.S. Pat. No. 3,479,395 reveals that olefins in oxygen may be converted to glycols and glycol acetates by being brought into contact with a solution comprising tellurium dioxide, an alkali metal halide and a redox agent dissolved in a solvent of certain specifications (water, acetic acid, dioxane, dialkyl formamides or dialkyl sulfoxides).

Further examples include U.S. Pat. No. 3,542,857 where vicinal glycol monoesters and diesters may be made by passing olefins in oxygen in an alkanoic acid medium over cerium salts. A method for making glycol esters from olefins and oxygen in a carboxylic acid medium over tellurium and an appropriate form of bromine is revealed in U.S. Pat. No. 3,668,239. Further, British Pat. No. 1,326,219 discloses that glycol esters may be produced from olefins and oxygen in the presence of at least one carboxylic acid when a halogen is employed as an anion and a metal cation is present which is selected from the group of tellurium, cerium, antimony, manganese, arsenic or cobalt. Other examples which reveal how esters may be made from olefins include U.S. Pat. No. 3,770,813 where an olefin with a chloro, hydroxy or lower alkanoyloxy substituent together with oxygen and a monobasic carboxylic acid may be reacted together over an iodide anion and a heavy metal cation of atomic numbers 21 to 30 and 48, and nitrogen-containing cations to give glycol esters. Olefins and oxygen may be reacted together over a catalyst system comprising a metal cation of tellurium, cerium, antimony, vanadium, gallium, arsenic, copper, selenium or silver with a bromine or chlorine anion to produce vicinal glycol esters which are later fractionated to give a residue with a boiling point higher than the vicinal glycol esters according to the disclosure in U.S. Pat. No. 3,789,065. The residue is then contacted with a carboxylic acid to yield additional vicinal glycol esters. British Pat. No. 1,353,814 describes the reaction of olefins and oxygen in a carboxylic acid in the liquid phase that contains at least 0.5 percent water over a catalyst system identical to that of the patent previously described to also yield vicinal glycol esters. Ethylene or propylene may be reacted with oxygen in a carboxylic acid over a catalyst system comprising a tellurium cation and a bromide anion or a selenium cation plus a chloride or bromide anion to produce vicinal glycol esters as revealed in U.S. Pat. No. 3,907,874.

Aliphatic hydrocarbon carboxylic acid esters of vicinal glycols which contain organic halogen impurities may be purified by passing them over aquobasic alkali metal compounds, aquobasic earth metal compounds or compounds (other than halides) of zinc, lead, cadmium, tin, mercury, silver, manganese, copper, nickel, cobalt, iron or chromium in accordance with the invention in British Pat. No. 1,410,834.

A system which has obtained a fair amount of commercial importance is described in U.S. Pat. No. 4,045,477 by which vicinal hydroxy esters and diesters are produced from olefins and oxygen over tellurium and an iodide source. Organic monoesters of vicinal glycols may also be produced from olefins, oxygen, water and a carboxylic acid over a system comprising an iodine compound (such as copper iodide, manganese iodide or cerium iodide), a copper compound, and an activated ion taken from the group of manganese, cerium, alkali metals, alkali earth metals, nitric compounds or mixtures thereof, according to the invention in U.S. Pat. No. 4,061,868. U.S. Pat. No. 4,069,381 reveals how glycol monoesters may be made from olefins, oxygen and carboxylic acids over a catalyst system where the cation is zirconium, niobium, molybdenum, hafnium, tantalum, tungsten or rhenium where the anion is a halide in the presence of lithium, sodium, potassium, titanium, vanadium, chromium, manganese, iron, cobalt, nickel, copper, zinc, aluminum or silver.

Some of the more recent patents in this field include the following. Esters may be produced from olefins in an acid plus oxygen over a tin or cerium catalyst in the presence of iodide as revealed by U.S. Pat. No. 4,154,957. Saturated vicinal esters may be produced from olefins, carboxylic acids and oxygen in the presence of a boron-containing catalyst according to the invention of U.S. Pat. No. 4,220,800. U.S. Pat. No. 4,221,916 teaches that olefins, carboxylic acids and oxygen when reacted together over a vanadium or ruthenium-containing catalyst can also produce saturated vicinal esters. U.S. Pat. No. 4,238,624 discloses a procedure by which ethylene, oxygen and a lower alkanoic acid are reacted together over an iodine source in a bismuth stabilized tellurium oxide catalyst on a carbon support to give ethylene glycol mono- and dialkanoates.

Further, alkylene glycol dicarboxylates may be made from carboxylic acid esters of monohydric or polyhydric short chain alcohols and olefins and oxygen over a catalyst system comprising tellurium, cerium, antimony, manganese, vanadium, gallium, arsenic or cobalt, plus a halogen anion and a hydrolyzing agent in addition to water as taught by U.S. Pat. No. 4,239,911.

No citations have been found to ester compounds similar to those disclosed herein.

SUMMARY OF THE INVENTION

The invention concerns novel cyclic compounds derived from 5-vinyl-2-norbornene, having the formula

  (I)

where $R^6$ is

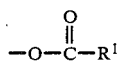

and $R^1$ is a lower alkyl group having 1 to 4 carbon atoms.

DETAILED DESCRIPTION OF THE PREFERRED EMBODIMENTS

Novel cyclic ester compounds of formula (I) may be prepared by the oxygen or air oxidation of 5-vinyl-2-norbornene in the presence of a carboxylic acid anhydride. The novel ester compounds of this invention may be represented by formula (I) where R is defined as noted. These ester compounds may serve as useful plasticizers, lubricants, solvents and fuel additives.

The compound 5-vinyl-2-norbornene has the empirical formula of $C_9H_{12}$ and the structural formula of

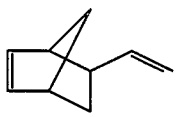  (II)

A second essential co-reactant is a carboxylic acid anhydride having the formula $$(R^1-\overset{O}{\underset{\|}{C}})_2O$$

where $R^1$ is a lower alkyl group of 1 to 4 carbon atoms. It is preferred that $R^1$ be an alkyl of from 1 to 3 carbon atoms, especially methyl.

Of course, molecular oxygen in a pure form or air is an essential co-reactant for the method of this invention.

While the reaction would occur with the application of heat alone, without a catalyst, it is preferred that a catalyst be employed. It is especially preferred that the catalyst be a metal borate compound such as an alkali metal borate, an alkali earth metal borate or a transition metal borate. Specific examples of transition metal borates, which are particularly preferred, include nickel borate, copper borate and iron borate. If a catalyst is employed, it should range from about 0.04 to 0.2 weight percent of the combined anhydride and cyclic olefin.

The reaction conditions under which the method for preparing the compounds of this invention may be conducted include a temperature range from 50° to 150° C. The pressure may be one atmosphere or higher. These conditions are much milder than many of the esterification reactions in the prior art discussed earlier. The mole ratio of anhydride to cyclic olefin should range from about 2:1 or more. An excess is preferable. Mixtures of these esters can also be created by using a mixture of anhydrides.

The invention will be further illustrated by the following example.

EXAMPLE 1

A small resin flask was fitted with a thermometer, mechanical stirrer, fritted glass addition tube and water cooled condenser. 5-vinyl-2-norbornene (25 ml), acetic anhydride (50 ml) and 0.05 g of nickel borate were charged to the flask. The mixture was heated to 110° C. and purged with air at 45 ml/min for 20 hours. The mixture was poured into water and shaken until all of the acetic anhydride had hydrolyzed. The aqueous layer was then drawn off and discarded. The organic layer was washed three times with water and the organic layer dried over anhydrous sodium sulfate.

An infrared spectrum showed a strong band at about 5.8 microns (C=O), and a weak band at about 6.1 microns (C=CH$_2$). Nuclear magnetic resonance analysis indicated that the reaction mixture was 60% diester. The remainder of the reaction mixture consisted of the norbornene and small amounts of unidentified material. There was not a significant amount of tetraester or vinyl diester.

The method used for making the novel esters of the invention may be used to make other esters and it may be expected that other methods could be used to produce the novel esters of this invention, which are defined only by the appended claims.

We claim:

1. Ester compounds having the formula

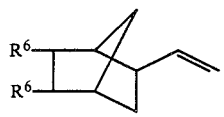

where $R^6$ is

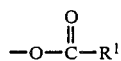

and $R^1$ is a lower alkyl group having 1 to 4 carbon atoms.

* * * * *